US00PP32569P2

(12) United States Plant Patent
Holtmaat

(10) Patent No.: US PP32,569 P2
(45) Date of Patent: Dec. 1, 2020

(54) ***RUDBECKIA* PLANT NAMED 'RUDBK166'**

(50) Latin Name: *Rudbeckia hirta*
Varietal Denomination: RUDBK166

(71) Applicant: Henricus Maria Joseph Holtmaat, Zuidwolde (NL)

(72) Inventor: Henricus Maria Joseph Holtmaat, Zuidwolde (NL)

(73) Assignee: NOVA PERENNE BV, Zuidwolde (NL)

( * ) Notice: Subject to any disclaimer, the term of this patent is extended or adjusted under 35 U.S.C. 154(b) by 0 days.

(21) Appl. No.: 16/873,153

(22) Filed: Feb. 15, 2020

(30) Foreign Application Priority Data

Dec. 31, 2019 (QZ) ..... PBR 2019/3525

(51) Int. Cl.
*A01H 5/02* (2018.01)
*A01H 6/14* (2018.01)

(52) U.S. Cl.
USPC ..... Plt./474

(58) Field of Classification Search
USPC ..... Plt./474
See application file for complete search history.

*Primary Examiner* — Susan McCormick Ewoldt
(74) *Attorney, Agent, or Firm* — Penny J. Aguirre

(57) ABSTRACT

A new cultivar of *Rudbeckia* plant named 'RUDBK166', characterized by its vigorous growth habit, its very floriferous blooming habit, its upright-mounded plant habit, and its inflorescences with ray florets that are yellow-orange in color and greyed-orange at the bases.

2 Drawing Sheets

Botanical classification: *Rudbeckia hirta.*
Variety denomination: 'RUDBK166'.

CROSS-REFERENCE TO RELATED APPLICATIONS

This application claims priority to European Community Plant Variety Office (CPVO) Plant Breeder's Rights Application No. 2019/3525 filed on Dec. 31, 2019, under 35 U.S.C. 119(f), the entire contents of which is incorporated by reference herein and is related to a co-pending U.S. Plant Patent Application filed for a plant derived from the same breeding program that is entitled *Rudbeckia* Plant Named 'RUDBR159' (U.S. Plant patent application Ser. No. 16/873,139).

BACKGROUND OF THE INVENTION

The present invention relates to a new and distinct cultivar of *Rudbeckia hirta* and will hereafter by referred to by its cultivar name, 'RUDBK166'. The new cultivar is an herbaceous perennial grown for use as a landscape plant.

'RUDBK166' was derived from a breeding program conducted by the Inventor at a nursery in Zuidwolde, The Netherlands. The objective of the breeding program was to select new cultivars of *Rudbeckia* with floriferous blooming habits and compact plant habits.

'RUDBK166' was selected in July of 2018 by the Inventor from amongst seedlings in a trial field that had been planted with seed derived from open pollination of numerous unpatented and unnamed proprietary plants from the Inventor's breeding program in July of 2017. The exact parentage is therefore unknown.

Asexual propagation of the new cultivar was first accomplished under the direction of the Inventor by tissue culture using meristematic tissue in Heerhugowaard, The Netherlands in March of 2019. Asexual propagation by tissue culture has determined that the characteristics of the new cultivar are stable and are reproduced true to type in successive generations.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosure may include but may not be limited to a website listing by AB-Cultivars (a company owned by the Inventor).

SUMMARY OF THE INVENTION

The following traits have been repeatedly observed and represent the characteristics of the new cultivar. These attributes in combination distinguish 'RUDBK166' as a unique cultivar of *Rudbeckia.*

1. 'RUDBK166' exhibits a vigorous growth habit.
2. 'RUDBK166' exhibits a very floriferous blooming habit.
3. 'RUDBK166' exhibits an upright-mounded plant habit.
4. 'RUDBK166' exhibits inflorescences with ray florets that are yellow-orange in color and greyed-orange at the bases.

'RUDBK166' can be compared to the *Rudbeckia* cultivars 'RUDBR159' and 'Giggling SmileyZ' (not patented). 'RUDBR159' is similar to 'RUDBK166' in having strong stems and in foliage color. 'RUDBR159' differs from 'RUDBK166' in having a taller and more narrow plant habit, disk florets that are larger in size and inflorescences with ray florets that are darker grey-orange to grey-red in color at the base. 'Giggling SmileyZ' is similar to 'RUDBK166' in plant height and in foliage color. 'Giggling SmileyZ' differs from 'RUDBK166' in having weaker stems and inflorescences with ray florets that are blackish grey-orange to grey-red in color at the bases.

BRIEF DESCRIPTION OF THE DRAWINGS

The accompanying colored photographs illustrate the overall appearance and distinct characteristics of the new *Rudbeckia*. The photographs were taken of a 6-month-old plant of 'RUDBK166' as grown outdoors in a 17-cm container in Zuidwolde, The Netherlands.

The photograph in FIG. 1 is a side view of 'RUDBK166' in bloom.

Figure 1:
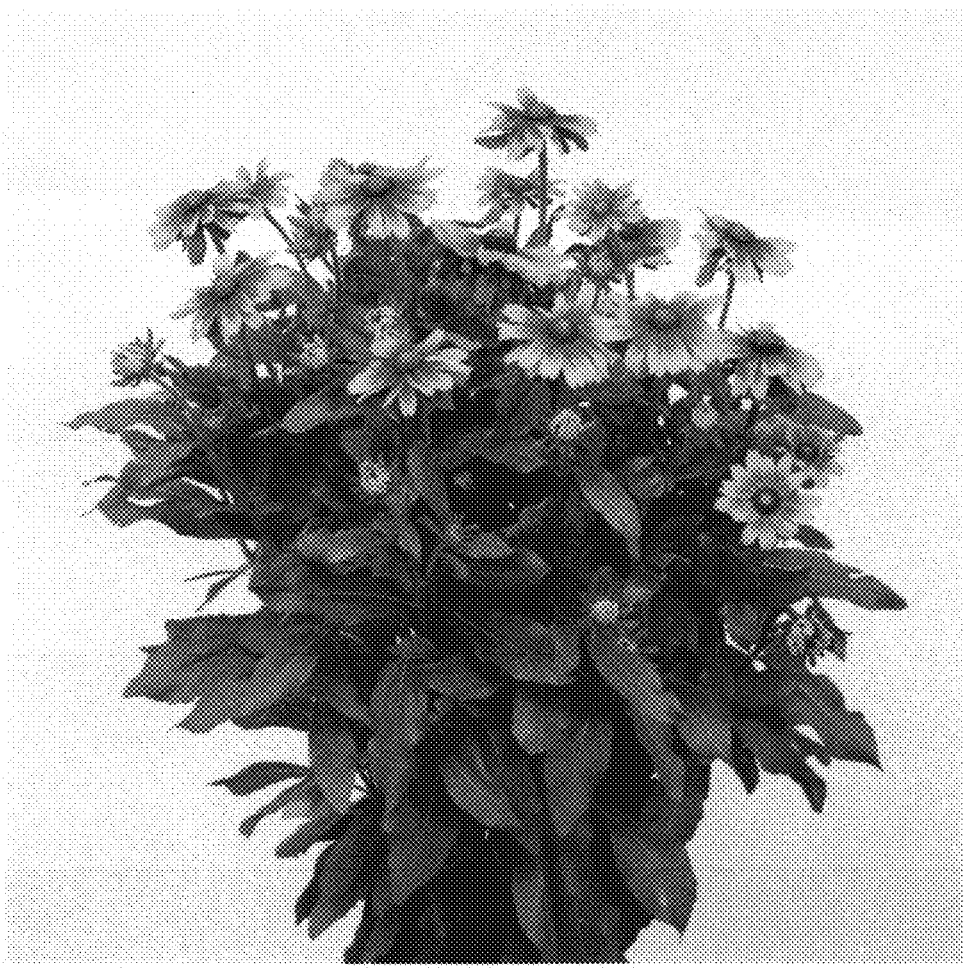
Figure 2:
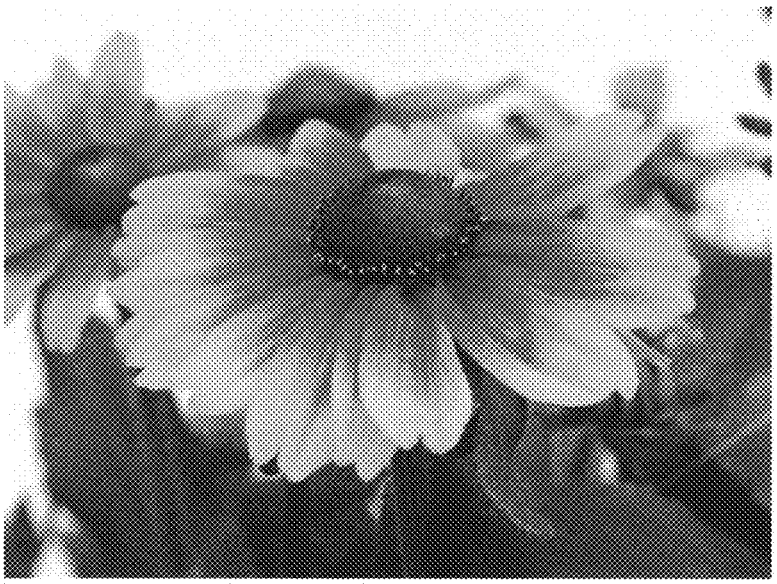

The photograph in FIG. 2 provides a close-up view of an inflorescences of 'RUDBK166'.

Figure 3:
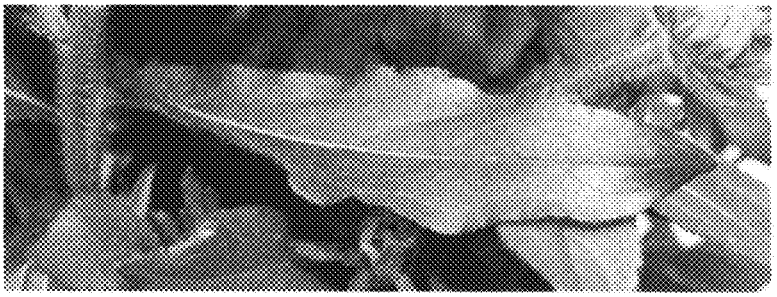

The photograph in FIG. 3 provides a close-up view of the foliage of 'RUDBK166'.

The colors in the photographs are as close as possible with the photographic and printing technology utilized and the color values cited in the detailed botanical description accurately describe the colors of the new *Rudbeckia*.

BOTANICAL DESCRIPTION OF THE PLANT

The following is a detailed description of 6-month-old plants of 'RUDBK166' as grown outdoors in 17-cm containers in Zuidwolde, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Average of 13 weeks from early summer to late summer in The Netherlands.

*Plant type*.—Perennial.

*Plant habit*.—Upright, compact.

*Plant shape*.—Obovate.

*Height and spread*.—Average of 65 cm in height from soil level to top of foliar plane and 74.4 cm in height from soil level to top of floral plane, 71 cm in diameter.

*Hardiness*.—At least in U.S.D.A. Zones 4 to 10.

*Diseases and pests*.—No susceptibility and resistance to diseases or pests has been observed.

*Root description*.—Fine and fibrous.

*Propagation*.—Tissue culture.

*Root development*.—An average of 3 weeks for root initiation with a young rooted plant produced in an average of 6 weeks.

*Growth rate and vigor*.—Vigorous.

Stem description:

*Stem shape*.—Moderately angled.

*Stem color*.—Young stems; 144A to 144B, mature stems; 145A to 145B, 144A to 144B at the angles.

*Stem size*.—An average of 8 mm in diameter and an average of 26 cm in height.

*Stem surface*.—Moderately glossy and densely covered with strigose hairs an average of 2 mm in length and close to NN155D in color.

*Stem number*.—Average of 14 main stems, 5 lateral branches per main stem.

*Internode length*.—An average of 5.8 cm in length.

*Stem aspect*.—Average of 30° to vertical.

*Branching*.—Freely branching from base with lateral stems.

Foliage description:

*Leaf shape*.—Obovate to narrowly obovate.

*Leaf division*.—Simple.

*Leaf base*.—Long cuneate in lower leaves to short cuneate or truncate in upper leaves.

*Leaf apex*.—Bluntly acute to narrowly obtuse.

*Leaf venation*.—Pinnate, color upper surface 148D, color lower surface 144A.

*Leaf margins*.—Un-deeply coarsely serrate, moderately undulate.

*Leaf attachment*.—Sessile.

*Leaf arrangement*.—Alternate.

*Leaf size*.—Average of 20.3 cm in length and 7.1 cm in width.

*Leaf color*.—Young upper surface; 137B, young lower surface; 138A and 138B, mature upper surface; 137A, mature lower surface; 138A and 147B.

*Leaf surface*.—Both surfaces very slightly glossy, rough to touch, lower surface is matte, slightly rugose, rough to touch, both surfaces densely pubescent with short strigose hairs; an average of 1.5 mm in length and 156D in color.

Flower description:

*Type*.—Terminal capitulum, consisting of ray florets and disk florets.

*Capitulum number*.—1 per stem, up to 90 per plant.

*Lastingness of inflorescence*.—Average of 2 weeks, persistent.

*Capitulum size*.—Matures to about 4.9 cm in height and 11.3 cm in diameter, disk size is an average of 2.9 cm in diameter.

*Fragrance*.—None.

*Involucral bracts (phyllaries)*.—Cuneate base, acute apex, oblanceolate to narrow oblong in shape, entire margins, average of 32 arranged in two rows, 3.6 cm in length and 9 mm in width, color; upper surface when fully open 137A, lower surface when fully open 138A, both surfaces and margins matte and densely covered with strigose hairs; an average of 1 mm in length and NN155D in color.

*Receptacle*.—Broad ovate in shape, an average of 1.3 cm in height and diameter, 157B in color.

*Buds*.—Globular in shape, immature ray florets pointed upward and curling inward, up to 2.7 cm in length and 5 cm in diameter, color; immature ray florets 153D, upper side of immature involucral bracts 137D, under side 138B, involucral bracts densely covered with strigose hairs; average length 2 mm, NN155D in color, immature ray floret surface densely covered with strigose hairs; average length 1 mm, 160D in color.

*Peduncle*.—Strong, straight on top of main flowering stem, average of 19.2 cm in length and 4.5 mm in diameter, color; 144A to 144B, surface moderately glossy sand densely covered with short strigose hairs; an average of 2 mm in length and NN155D in color.

*Ray florets*.—Average of 18 (varying between 17 and 20), rotate around the disk, oblong in shape, average of 4.9 cm in length and 2 cm in width, emarginate apex, cuneate base, entire margin, both surfaces are velvety, matte and glabrous, lower surface moderately covered with very short adpressed strigose hairs, average of 7 mm in length and 160D in color, held near horizontal, color; when opening upper surface; lower half 175B, upper half 17B, when opening lower surface; 13B, lower half tinged 195B, when fully open upper and lower surface and veins; lower ⅗th 178A, upper ⅖th 17A, when fully open lower surface; 13B, changing to 146D at the base.

*Disk flowers*.—Average of 800, tubular, 22 whorls arranged spirally on a conical receptacle, lower 90% fused into tube, upper 10% free, about 8 mm in length and 4 mm in width, free lobes have entire margins and are curled backwards, both surfaces glabrous and moderately glossy, color; when opening upper and lower surface; 200B, mid-section 200B, tinged N186C, base 155A, when fully open upper and lower surface; top; between 200A and 203A, mid-section; in between N186C and 200B, base; 155A, spines; none, bracts, 1 per disk floret, soft, flattened, an average of 7 mm in length and 1 mm in diameter, oblanceolate in shape, acute apex, narrow cuneate base, color apex; 178A, mid-section; 145B, margins 178A, base 157A.

Reproductive organs:

*Gynoecium*.—Pistil; 1, 6 mm in length, style; 5 mm in length, color; 200A, mid-section 187A, base 155C, stigma; cleft, decurrent, 4 mm in diameter, 200A in color, ovary; NN155A in color.

*Androecium*.—Stamens; 5, filaments; 3 mm in length, 157A in color, anther; narrow oblong in shape, 2 mm in length, 0.5 mm in width, 200A in color, pollen; moderate in quantity and 15A in color.

*Fruit/seed*.—None observed to date.

It is claimed:

1. A new and distinct cultivar of *Rudbeckia* plant named 'RUDBK166' substantially as herein illustrated and described.

* * * * *